(12) United States Patent
Belyea et al.

(10) Patent No.: US 7,098,029 B1
(45) Date of Patent: Aug. 29, 2006

(54) PRODUCT AND METHOD FOR CONTROL OF OBESITY

(75) Inventors: Christopher Ian Belyea, Elsternwick (AU); Frank Man-Woon Ng, Kew (AU); Paul Vaughan, Toorak (AU)

(73) Assignee: Metabolic Pharmaceuticals Limited, Toorak (AU)

( * ) Notice: Subject to any disclaimer, the term of this patent is extended or adjusted under 35 U.S.C. 154(b) by 338 days.

(21) Appl. No.: 10/129,205

(22) PCT Filed: Nov. 6, 2000

(86) PCT No.: PCT/AU00/01362

§ 371 (c)(1),
(2), (4) Date: Oct. 21, 2002

(87) PCT Pub. No.: WO01/33977

PCT Pub. Date: May 17, 2001

(30) Foreign Application Priority Data

Nov. 5, 1999 (AU) .................................. PQ3875

(51) Int. Cl.
*C12N 5/10* (2006.01)
*C12N 15/29* (2006.01)
*A23L 1/00* (2006.01)
*A01H 1/00* (2006.01)

(52) U.S. Cl. ..................... 435/419; 435/468; 800/288; 800/278; 99/275

(58) Field of Classification Search ................ 800/288, 800/278, 295, 298
See application file for complete search history.

(56) References Cited

U.S. PATENT DOCUMENTS

| 5,869,452 A | 2/1999 | Ng et al. |
| 6,335,319 B1 | 1/2002 | Ng et al. |

FOREIGN PATENT DOCUMENTS

| AU | 77727/94 | | 5/1996 |
| AU | PCT/AU98/00724 | * | 3/1999 |
| CA | 2252059 | | 11/2002 |
| EP | 0377540 | | 7/1990 |
| WO | WO 90/15142 | | 12/1990 |
| WO | WO 96/11704 | | 4/1996 |
| WO | WO 97/27298 | | 7/1997 |
| WO | WO 97/32986 | | 9/1997 |
| WO | WO 99/12969 | | 3/1999 |
| WO | WO 01/72770 | | 10/2001 |
| WO | WO 02/18436 | | 3/2002 |

OTHER PUBLICATIONS

Lehninger AL, Nelson DL, and Cox MM. (1993) Principles of Biochemistry with an Extended Discussion of Oxygen-Binding Proteins. Worth Publishers, New York, NY.*
Li B-J, Wang J-F, Xu Z-F, Xu Y-Q, Yu M-Z, He X, and Shen Y. (1993) Integration and Expression of Human Growth Hormone Gene in Caladium Bicolor. Science in China, Series B, vol. 37, pp. 280-285.*
Ben-Atia et al., "Preparation of recombinant gilthead seabream (Sparas aurata) growth hormone and its use for stimulation of larvae growth by oral administration," *Gen. Comp. Endocrinol.* 113(1):155-164, Jan. 1999.
Boeuf et al., "Control of the somatic growth in turbot," *J. Fish Biology* 55(a):128-147, 1999.
Pinkert et al., "Characterization of transgenic livestock production," *Domest. Anim. Endocrinol.* 7(1):1-18, Jan. 1990.
Solomon et al., "Biotechnology for porcine products and its effect on meat products," *Food Chemistry* 59(4):499-504, Aug. 1997.
Kim and Peppas, "Poly(ethylene glycol)-containing Hydrogels for Oral Protein Delivery Applications," *Biomedical Microdevices* 5(4):333-341 (2003).
Soltero and Ekwuribe, "The oral delivery of protein and peptide drugs," *Innov in Pharm Tech.* 106-110 (2001).
Woodley, "Enzymatic barriers for GI peptide and protein delivery," *Crit Rev Ther Drug Carrier Syst.* 11(2-3):61-95 (1994) *Abstract Only*.
McIntosh, Report Excerpt entitled "The Oral Delivery of AOD9406 in a GM seed fed to pig," *Metabolic Pharmaceuticals Ltd.*, Report No. MBP Jan. 8, 2003—AOD9604, 5 pages (Finalized: Sep. 4, 2003).
http://www.3.interscience.wiley.com/cgi-bin/abstract/72505066/
ABSTRACT: Fix, "Strategies for delivery of peptides utilizing absorption-enhancing agents," Abstract (DOI 10.1021/js960158a), from Papers from the Conference on Formulations and Drug Delivery, conference held Oct. 10-13, 1995 Boston MA (1 page; published on-line Jun. 12, 2000).

* cited by examiner

*Primary Examiner*—Ashwin D. Mehta
*Assistant Examiner*—Cathy Kingdon Worley
(74) *Attorney, Agent, or Firm*—Klarquist Sparkman, LLP

(57) ABSTRACT

The invention relates to food and beverage products which are useful in control of obesity. The food or beverage comprises or is made by a transgenic plant or parts thereof comprising a nucleic acid molecule, the nucleic acid molecule encoding a C-terminal growth hormone fragment which has the ability to modulate lipid metabolism. The transgenic plant may be used in a production of a fermented food or beverage product, or may be a part of an edible plant, such as a fruit or vegetable, including but not limited to tomato, banana, and potato.

18 Claims, No Drawings

SEQUENCE LISTING

<160> NUMBER OF SEQ ID NOS: 40

<210> SEQ ID NO 1
<211> LENGTH: 61
<212> TYPE: DNA
<213> ORGANISM: Saccharomyces cerevisiae

<400> SEQUENCE: 1
aattcatgta cttcagaatt gttcaatgta gatccgttga aggttcttgt ggtttctaac      60
g                                                                     61

<210> SEQ ID NO 2
<211> LENGTH: 61
<212> TYPE: DNA
<213> ORGANISM: Saccharomyces cerevisiae

<400> SEQUENCE: 2
ggccgcttag aaaccacaag aaccttcaac aggtctacat tgaacaattc tgaagtacat      60
g                                                                     61

<210> SEQ ID NO 3
<211> LENGTH: 60
<212> TYPE: DNA
<213> ORGANISM: Saccharomyces cerevisiae

<400> SEQUENCE: 3
aattcatgta cttcagaatt gttcaatgta gatccgttga aggttcttgt ggtttctaag      60

<210> SEQ ID NO 4
<211> LENGTH: 60
<212> TYPE: DNA
<213> ORGANISM: Saccharomyces cerevisiae

<400> SEQUENCE: 4
gatccttaga aaccacaaga accttcaaca ggtctacatt gaacaattct gaagtacatg      60

<210> SEQ ID NO 5
<211> LENGTH: 60
<212> TYPE: DNA
<213> ORGANISM: Saccharomyces cerevisiae

<400> SEQUENCE: 5
gatccatgta cttcagaatt gttcaatgta gatccgttga aggttcttgt ggtttctaag      60

<210> SEQ ID NO 6
<211> LENGTH: 60
<212> TYPE: DNA
<213> ORGANISM: Saccharomyces cerevisiae

<400> SEQUENCE: 6
aattcttaga aaccacaaga accttcaaca ggtctacatt gaacaattct gaagtacatg      60

<210> SEQ ID NO 7
<211> LENGTH: 60
<212> TYPE: DNA
<213> ORGANISM: Saccharomyces cerevisiae

<400> SEQUENCE: 7
aattcatgta cttcagaatt gttcaatgta gatccgttga aggttcttgt ggtttctaag      60

<210> SEQ ID NO 8
<211> LENGTH: 60
<212> TYPE: DNA
<213> ORGANISM: Saccharomyces cerevisiae

<400> SEQUENCE: 8
tcgacttaga aaccacaaga accttcaaca ggtctacatt gaacaattct gaagtacatg      60

<210> SEQ ID NO 9
<211> LENGTH: 16
<212> TYPE: PRT
<213> ORGANISM: Artificial
<220> FEATURE:
<223> OTHER INFORMATION: Synthetic Peptide

<400> SEQUENCE: 9

Tyr Leu Arg Ile Val Gln Cys Arg Ser Val Glu Gly Ser Cys Gly Phe
1               5                   10                  15

<210> SEQ ID NO 10
<211> LENGTH: 8
<212> TYPE: PRT
<213> ORGANISM: Artificial
<220> FEATURE:
<223> OTHER INFORMATION: epitope tag sequence FLAG; synthetic peptide

<400> SEQUENCE: 10

Asp Tyr Lys Asp Asp Asp Asp Lys
1               5

<210> SEQ ID NO 11
<211> LENGTH: 61
<212> TYPE: DNA
<213> ORGANISM: Artificial
<220> FEATURE:
<223> OTHER INFORMATION: Synthetic Oligonucleotide

<400> SEQUENCE: 11
ggccgcttag aaaccacaag aaccttcaac ggatctacat tgaacaattc tgaagtacat      60
g                                                                     61

<210> SEQ ID NO 12
<211> LENGTH: 60
<212> TYPE: DNA
<213> ORGANISM: Artificial
<220> FEATURE:
<223> OTHER INFORMATION: Synthetic Oligonucleotide

<400> SEQUENCE: 12
aattcatgta cttcagaatt gttcaatgta gatccgttga aggttcttgt ggtttctaag      60

<210> SEQ ID NO 13
<211> LENGTH: 60
<212> TYPE: DNA
<213> ORGANISM: Artificial
<220> FEATURE:
<223> OTHER INFORMATION: Synthetic Oligonucleotide

<400> SEQUENCE: 13
gatccttaga aaccacaaga accttcaacg gatctacatt gaacaattct gaagtacatg      60

<210> SEQ ID NO 14
<211> LENGTH: 60
<212> TYPE: DNA
<213> ORGANISM: Artificial
<220> FEATURE:

```
<223> OTHER INFORMATION: Synthetic Oligonucleotide

<400> SEQUENCE: 14
gatccatgta cttcagaatt gttcaatgta gatccgttga aggttcttgt ggtttctaag      60

<210> SEQ ID NO 15
<211> LENGTH: 60
<212> TYPE: DNA
<213> ORGANISM: Artificial
<220> FEATURE:
<223> OTHER INFORMATION: Synthetic Oligonucleotide

<400> SEQUENCE: 15
aattcttaga aaccacaaga accttcaacg gatctacatt gaacaattct gaagtacatg      60

<210> SEQ ID NO 16
<211> LENGTH: 60
<212> TYPE: DNA
<213> ORGANISM: Artificial
<220> FEATURE:
<223> OTHER INFORMATION: Synthetic Oligonucleotide

<400> SEQUENCE: 16
aattcatgta cttcagaatt gttcaatgta gatccgttga aggttcttgt ggtttctaag      60

<210> SEQ ID NO 17
<211> LENGTH: 60
<212> TYPE: DNA
<213> ORGANISM: Artificial
<220> FEATURE:
<223> OTHER INFORMATION: Synthetic Oligonucleotide

<400> SEQUENCE: 17
tcgacttaga aaccacaaga accttcaacg gatctacatt gaacaattct gaagtacatg      60

<210> SEQ ID NO 18
<211> LENGTH: 61
<212> TYPE: DNA
<213> ORGANISM: Artificial
<220> FEATURE:
<223> OTHER INFORMATION: Synthetic Oligonucleotide

<400> SEQUENCE: 18
aattcatgta cttcagaatt gttcaatgta gatccgttga aggttcttgt ggtttctaag      60
c                                                                     61

<210> SEQ ID NO 19
<211> LENGTH: 27
<212> TYPE: PRT
<213> ORGANISM: Artificial
<220> FEATURE:
<223> OTHER INFORMATION: synthetic peptide

<400> SEQUENCE: 19

Asp Tyr Lys Asp Asp Asp Asp Lys Glu Phe Met Tyr Leu Arg Ile Val
1               5                   10                  15

Gln Cys Arg Ser Val Glu Gly Ser Cys Gly Phe
            20                  25

<210> SEQ ID NO 20
<211> LENGTH: 15
<212> TYPE: PRT
<213> ORGANISM: Artificial
<220> FEATURE:
<223> OTHER INFORMATION: hGH 177-191 with Lysine at 179; cyclic
```

```
        peptide
<220> FEATURE:
<221> NAME/KEY: DISULFID
<222> LOCATION: (6)..(13)

<400> SEQUENCE: 20

Leu Arg Lys Val Gln Cys Arg Ser Val Glu Gly Ser Cys Gly Phe
1               5                   10                  15

<210> SEQ ID NO 21
<211> LENGTH: 15
<212> TYPE: PRT
<213> ORGANISM: Artificial
<220> FEATURE:
<223> OTHER INFORMATION: hGH 177-191 with CONH2 replacing COOH; cyclic
        peptide
<220> FEATURE:
<221> NAME/KEY: DISULFID
<222> LOCATION: (6)..(13)
<220> FEATURE:
<221> NAME/KEY: MOD_RES
<222> LOCATION: (15)..(15)
<223> OTHER INFORMATION: CONH2 replaces COOH

<400> SEQUENCE: 21

Leu Arg Ile Val Gln Cys Arg Ser Val Glu Gly Ser Cys Gly Phe
1               5                   10                  15

<210> SEQ ID NO 22
<211> LENGTH: 15
<212> TYPE: PRT
<213> ORGANISM: Artificial
<220> FEATURE:
<223> OTHER INFORMATION: hGH 177-191 with CH3CO-NH replacing NH2;
        cyclic peptide
<220> FEATURE:
<221> NAME/KEY: MOD_RES
<222> LOCATION: (1)..(1)
<223> OTHER INFORMATION: CH3CO-NH replaces NH2
<220> FEATURE:
<221> NAME/KEY: DISULFID
<222> LOCATION: (6)..(13)

<400> SEQUENCE: 22

Leu Arg Ile Val Gln Cys Arg Ser Val Glu Gly Ser Cys Gly Phe
1               5                   10                  15

<210> SEQ ID NO 23
<211> LENGTH: 15
<212> TYPE: PRT
<213> ORGANISM: Artificial
<220> FEATURE:
<223> OTHER INFORMATION: hGH 177-191 with Lysine at 183; cyclic peptide
<220> FEATURE:
<221> NAME/KEY: DISULFID
<222> LOCATION: (6)..(13)

<400> SEQUENCE: 23

Leu Arg Ile Val Gln Cys Lys Ser Val Glu Gly Ser Cys Gly Phe
1               5                   10                  15

<210> SEQ ID NO 24
<211> LENGTH: 15
<212> TYPE: PRT
<213> ORGANISM: Artificial
<220> FEATURE:
<223> OTHER INFORMATION: hGH 177-191 with Lysine at 183 and amide bond
        between 183 and 186; bicyclic peptide
<220> FEATURE:
<221> NAME/KEY: DISULFID
<222> LOCATION: (6)..(13)
```

```
<220> FEATURE:
<221> NAME/KEY: MISC_FEATURE
<222> LOCATION: (7)..(10)
<223> OTHER INFORMATION: Amide bond

<400> SEQUENCE: 24

Leu Arg Ile Val Gln Cys Lys Ser Val Glu Gly Ser Cys Gly Phe
1               5                   10                  15

<210> SEQ ID NO 25
<211> LENGTH: 15
<212> TYPE: PRT
<213> ORGANISM: Artificial
<220> FEATURE:
<223> OTHER INFORMATION: hGH 177-191 with H replacing NH2; cyclic
      peptide
<220> FEATURE:
<221> NAME/KEY: MOD_RES
<222> LOCATION: (1)..(1)
<223> OTHER INFORMATION: H replaces NH2
<220> FEATURE:
<221> NAME/KEY: DISULFID
<222> LOCATION: (6)..(13)

<400> SEQUENCE: 25

Leu Arg Ile Val Gln Cys Arg Ser Val Glu Gly Ser Cys Gly Phe
1               5                   10                  15

<210> SEQ ID NO 26
<211> LENGTH: 15
<212> TYPE: PRT
<213> ORGANISM: Artificial
<220> FEATURE:
<223> OTHER INFORMATION: hGH 177-191 with D-Alanine at 187 and 190;
      cyclic peptide
<220> FEATURE:
<221> NAME/KEY: DISULFID
<222> LOCATION: (6)..(13)
<220> FEATURE:
<221> NAME/KEY: Xaa
<222> LOCATION: (11)..(11)
<223> OTHER INFORMATION: D-Alanine
<220> FEATURE:
<221> NAME/KEY: Xaa
<222> LOCATION: (14)..(14)
<223> OTHER INFORMATION: D-Alanine

<400> SEQUENCE: 26

Leu Arg Ile Val Gln Cys Arg Ser Val Glu Xaa Ser Cys Xaa Phe
1               5                   10                  15

<210> SEQ ID NO 27
<211> LENGTH: 15
<212> TYPE: PRT
<213> ORGANISM: Artificial
<220> FEATURE:
<223> OTHER INFORMATION: hGH 177-191 with Penicillamine at 182 and 189;
      Pen bond between 182 and 189; cyclic peptide
<220> FEATURE:
<221> NAME/KEY: Xaa
<222> LOCATION: (6)..(6)
<223> OTHER INFORMATION: Penicillamine
<220> FEATURE:
<221> NAME/KEY: Xaa
<222> LOCATION: (13)..(13)
<223> OTHER INFORMATION: Penicillamine

<400> SEQUENCE: 27

Leu Arg Ile Val Gln Xaa Arg Ser Val Glu Gly Ser Xaa Gly Phe
1               5                   10                  15
```

```
<210> SEQ ID NO 28
<211> LENGTH: 15
<212> TYPE: PRT
<213> ORGANISM: Artificial
<220> FEATURE:
<223> OTHER INFORMATION: hGH 177-191 with Alanine at 191; cyclic peptide
<220> FEATURE:
<221> NAME/KEY: DISULFID
<222> LOCATION: (6)..(13)

<400> SEQUENCE: 28

Leu Arg Ile Val Gln Cys Arg Ser Val Glu Gly Ser Cys Gly Ala
1               5                   10                  15

<210> SEQ ID NO 29
<211> LENGTH: 15
<212> TYPE: PRT
<213> ORGANISM: Artificial
<220> FEATURE:
<223> OTHER INFORMATION: hGH 177-191 with Alanine at 190; cyclic peptide
<220> FEATURE:
<221> NAME/KEY: DISULFID
<222> LOCATION: (6)..(13)

<400> SEQUENCE: 29

Leu Arg Ile Val Gln Cys Arg Ser Val Glu Gly Ser Cys Ala Phe
1               5                   10                  15

<210> SEQ ID NO 30
<211> LENGTH: 16
<212> TYPE: PRT
<213> ORGANISM: Artificial
<220> FEATURE:
<223> OTHER INFORMATION: Tyrosine - hGH 177-191; cyclic peptide
<220> FEATURE:
<221> NAME/KEY: DISULFID
<222> LOCATION: (7)..(14)

<400> SEQUENCE: 30

Tyr Leu Arg Ile Val Gln Cys Arg Ser Val Glu Gly Ser Cys Gly Phe
1               5                   10                  15

<210> SEQ ID NO 31
<211> LENGTH: 16
<212> TYPE: PRT
<213> ORGANISM: Artificial
<220> FEATURE:
<223> OTHER INFORMATION: Lysine - hGH 177-191; cyclic peptide
<220> FEATURE:
<221> NAME/KEY: DISULFID
<222> LOCATION: (7)..(14)

<400> SEQUENCE: 31

Lys Leu Arg Ile Val Gln Cys Arg Ser Val Glu Gly Ser Cys Gly Phe
1               5                   10                  15

<210> SEQ ID NO 32
<211> LENGTH: 15
<212> TYPE: PRT
<213> ORGANISM: Artificial
<220> FEATURE:
<223> OTHER INFORMATION: hGH 177-191 with Alanine at 177; cyclic peptide
<220> FEATURE:
<221> NAME/KEY: DISULFID
<222> LOCATION: (6)..(13)

<400> SEQUENCE: 32

Ala Arg Ile Val Gln Cys Arg Ser Val Glu Gly Ser Cys Gly Phe
1               5                   10                  15
```

```
<210> SEQ ID NO 33
<211> LENGTH: 15
<212> TYPE: PRT
<213> ORGANISM: Artificial
<220> FEATURE:
<223> OTHER INFORMATION: hGH 177-191 with Alanine at 179; cyclic peptide
<220> FEATURE:
<221> NAME/KEY: DISULFID
<222> LOCATION: (6)..(13)

<400> SEQUENCE: 33

Leu Arg Ala Val Gln Cys Arg Ser Val Glu Gly Ser Cys Gly Phe
1               5                   10                  15

<210> SEQ ID NO 34
<211> LENGTH: 15
<212> TYPE: PRT
<213> ORGANISM: Artificial
<220> FEATURE:
<223> OTHER INFORMATION: hGH 177-191 with Alanine at 180; cyclic peptide
<220> FEATURE:
<221> NAME/KEY: DISULFID
<222> LOCATION: (6)..(13)

<400> SEQUENCE: 34

Leu Arg Ile Ala Gln Cys Arg Ser Val Glu Gly Ser Cys Gly Phe
1               5                   10                  15

<210> SEQ ID NO 35
<211> LENGTH: 15
<212> TYPE: PRT
<213> ORGANISM: Artificial
<220> FEATURE:
<223> OTHER INFORMATION: hGH 177-191 with Alanine at 181; cyclic peptide
<220> FEATURE:
<221> NAME/KEY: DISULFID
<222> LOCATION: (6)..(13)

<400> SEQUENCE: 35

Leu Arg Ile Val Ala Cys Arg Ser Val Glu Gly Ser Cys Gly Phe
1               5                   10                  15

<210> SEQ ID NO 36
<211> LENGTH: 15
<212> TYPE: PRT
<213> ORGANISM: Artificial
<220> FEATURE:
<223> OTHER INFORMATION: hGH 177-191 with Alanine at 184; cyclic peptide
<220> FEATURE:
<221> NAME/KEY: DISULFID
<222> LOCATION: (6)..(13)

<400> SEQUENCE: 36

Leu Arg Ile Val Gln Cys Arg Ala Val Glu Gly Ser Cys Gly Phe
1               5                   10                  15

<210> SEQ ID NO 37
<211> LENGTH: 15
<212> TYPE: PRT
<213> ORGANISM: Artificial
<220> FEATURE:
<223> OTHER INFORMATION: hGH 177-191 with Alanine at 185; cyclic peptide
<220> FEATURE:
<221> NAME/KEY: DISULFID
<222> LOCATION: (6)..(13)
```

```
<400> SEQUENCE: 37

Leu Arg Ile Val Gln Cys Arg Ser Ala Glu Gly Ser Cys Gly Phe
1               5                   10                  15

<210> SEQ ID NO 38
<211> LENGTH: 15
<212> TYPE: PRT
<213> ORGANISM: Artificial
<220> FEATURE:
<223> OTHER INFORMATION: hGH 177-191 with Alanine at 187; cyclic peptide
<220> FEATURE:
<221> NAME/KEY: DISULFID
<222> LOCATION: (6)..(13)

<400> SEQUENCE: 38

Leu Arg Ile Val Gln Cys Arg Ser Val Glu Ala Ser Cys Gly Phe
1               5                   10                  15

<210> SEQ ID NO 39
<211> LENGTH: 15
<212> TYPE: PRT
<213> ORGANISM: Artificial
<220> FEATURE:
<223> OTHER INFORMATION: hGH 177-191 with Alanine at 188; cyclic peptide
<220> FEATURE:
<221> NAME/KEY: DISULFID
<222> LOCATION: (6)..(13)

<400> SEQUENCE: 39

Leu Arg Ile Val Gln Cys Arg Ser Val Glu Gly Ala Cys Gly Phe
1               5                   10                  15

<210> SEQ ID NO 40
<211> LENGTH: 17
<212> TYPE: PRT
<213> ORGANISM: Artificial
<220> FEATURE:
<223> OTHER INFORMATION: Lysine - Lysine - hGH 177-191; cyclic peptide
<220> FEATURE:
<221> NAME/KEY: DISULFID
<222> LOCATION: (8)..(15)

<400> SEQUENCE: 40

Lys Lys Leu Arg Ile Val Gln Cys Arg Ser Val Glu Gly Ser Cys Gly
1               5                   10                  15

Phe
```

PRODUCT AND METHOD FOR CONTROL OF OBESITY

CROSS REFERENCE TO RELATED APPLICATIONS

This is the U.S. national stage of PCT Application No. PCT/AU00/01362 filed Nov. 6, 2000, (published in English under PCT Article 21(2)), which in turn claims the benefit of Australian Application No. PQ 3875 filed Nov. 5, 1999. Both applications are incorporated herein in their entirety.

This invention relates to the prevention and treatment of obesity in mammals, including humans. In particular, the invention relates to novel food and beverage products, which are useful in the control of obesity via the regulation of lipid and carbohydrate metabolism. The invention is applicable to both human and veterinary medicine and in animal husbandry.

BACKGROUND OF THE INVENTION

In Australian patent No. 693478 (U.S. Pat. No. 5,869,452) by Monash University, we described the use of a peptide derived from the carboxyl-terminal sequence of human growth hormone, or corresponding regions from growth hormone of other mammalian species, for the control of obesity. This region of growth hormone has the ability to modulate lipid metabolism. In particular, a synthetic peptide corresponding to amino acid residues 177–191 of the human growth hormone sequence (hereinafter referred to as hGH 177–191) was found to reduce body weight gain and adipose tissue mass in a model system for obesity, the C57B1/6J (Ob/Ob) mouse. A subsequent application, PCT/AU98/00724 (U.S. Pat. No. 6,737,407) by Metabolic Pharmaceuticals Ltd, discloses analogues of the hGH177–191 peptide which share this activity. The entire disclosure of U.S. Pat. No. 5,869,452 and (U.S. Pat. No. 6,737,407) are incorporated herein by this reference. All of the studies described in the two earlier specifications were carried out using administration of the peptide by injection.

Our subsequent discovery that these peptides are orally active, possess no known toxicity at any dose, and can be effectively administered at frequencies ranging from once every few days to continuously has led to the concept that, counterintuitively, a fat-reducing food, beverage, or food additive may be produced. In particular, the peptide may be expressed directly by microorganisms which are utilised in production of food products, such as fermentative microorganisms used in the production of beverages such as beer, wine and cider, fermented milk products such as yoghurts and buttermilks, probiotic foods, or fermented meat products such as salami, and baked goods such as breads, including sourdough breads. The peptide may also be expressed in fruit and vegetable plants, such as bananas, tomatoes, or potatoes.

The recognition by the inventors is that the above-mentioned features of the peptides make possible the provision of the growth hormone fragment in a food or beverage product by recombinant DNA methods, thus providing a reliable source of sufficient quantities of the growth hormone fragment in a convenient, inexpensive form for use in various prophylactic and therapeutic applications or in improvement of meat quality, without the necessity for costly purification procedures. In view of the advantageous biological properties of the growth hormone fragment, recombinant organisms expressing the growth hormone fragment are especially useful in a variety of circumstances where it is necessary or desirable to maintain control of weight or of food utilization.

SUMMARY OF THE INVENTION

According to a first aspect, the invention provides a recombinant organism, comprising an exogenous nucleic acid molecule which encodes a growth hormone polypeptide having improved properties in modulating lipid metabolism, with the proviso that the exogenous nucleic acid molecule does not encode an intact, full-length mammalian growth hormone.

For the purposes of this specification, the term "growth hormone fragment" or "growth hormone polypeptide" is to be understood to mean a polypeptide fragment from the carboxy-terminal region of the amino acid sequence of a mammalian growth hormone, which has one or more of the following biological activities:

(a) ability to reduce body weight gain and adipose tissue mass in a homologous mammal,
(b) ability to reduce lipogenic activity, and
(c) ability to stimulate lipolysis.

Preferably the growth hormone fragment has the ability to stimulate the activity of hormone-sensitive lipase, a key enzyme in lipolysis, and to inhibit acetyl CoA carboxylase, a key enzyme in lipogenesis.

Preferably the growth hormone fragment comprises at least the disulphide-bonded loop of a mammalian growth hormone.

The term "growth hormone fragment" also encompasses peptides which are analogues of the native carboxy-terminal sequences of mammalian growth hormones, provided that the analogue retains one or more of the biological activities referred to above. Such analogues may be derived from natural sources, produced by recombinant DNA technology, or synthesised using conventional peptide synthetic methods. Such peptides synthetic methods are to be understood to include combinatorial methods. Preferably such analogues include a disulphide bond which confers a cyclic configuration on the peptide. In particular, all of the peptides disclosed in PCT/AU98/00724 (U.S. Pat. No. 6,737,407) are to be understood to be within the scope of this invention. These peptides include those set forth herein as SEQ ID NOS: 20–40.

Preferably the first nucleic acid segment encodes amino acids 182–189 (hGH 182–189), more preferably amino acids 177–191 of human growth hormone (hGH 177–191). However, it will be clearly understood that the invention is also applicable to growth hormone fragments derived from growth hormones of other mammalian species, including but not limited to those of domestic mammals such as cattle, sheep, pigs and horses, companion animals such as cats and dogs, and zoo animals including felids, canids, and non human primates. There is strong conservation of the sequence of this region of growth hormone across species, as set out in PCT/AU98/00724 (U.S. Pat. No. 6,737,407) and references cited therein.

Where a fusion partner is used, this will preferably be a signal sequence for a secreted polypeptide or protein, and more preferably will include a specific protease cleavage site between the fusion partner and the growth hormone fragment. Where an epitope tag is used, this facilitates isolation of the growth hormone fragment from the organism.

In one embodiment, the invention provides a host cell, transformed with a nucleic acid molecule according to the invention. The host cell may be a microorganism used in production of a fermented food or beverage product, or may be a cell of an edible plant, such as a fruit or vegetable, including but not limited to tomato, banana, and potato. Alternatively the host cell may be a cell of a transgenic non-human mammal, such as a cow, sheep or goat, which secretes the growth hormone fragment into its milk.

The nucleic acid molecules of the invention may be expressed in plant cells. In expressing the nucleic acid molecule of the invention in plants, the expressed protein may in principle be located in any desired compartment within the plant cell. In order to locate the protein within a specific compartment, the coding region is optionally linked to DNA sequences which ensure localization in the desired compartment. Such sequences are known; see for example Braun et al., EMBO J. 11 (1992), 3219–3227; Wolter et al., Proc. Natl. Acad. Sci. USA 85 (1988), 846–850; Sonnewald et al., Plant J. 1 (1991), 95–106.

Thus the invention also provides transgenic plant cells transformed and genetically modified with a nucleic acid molecule of the invention, as well as transgenic plant cells which are derived from cells transformed in such a way. Such cells comprise a nucleic acid molecule of the invention, which is preferably linked to one or more regulatory DNA elements which ensure the transcription in plant cells; preferably the regulatory element is a promoter.

The transgenic plant cells can be regenerated to whole plants, using methods known to the person skilled in the art. Thus plants obtained by regenerating the transgenic plant cells of the invention and plants which contain the transgenic plant cells of the invention are also within the scope of the present invention. The transgenic plants may in principle be plants of any desired species, i.e. they may be monocotyledonous as well as dicotyledonous plants. They are preferably edible plants, in particular starch-synthesizing or starch-storing plants such as cereals, including rye, barley, oats, wheat, rice, maize etc., peas, cassava, potatoes, fruits such as banana, or vegetables such as tomato. Plants used as animal feed, either with or without prior processing, may also be used. Such plants include canola, which is widely used in the form of canola meal.

The invention also relates to propagation material of the plants of the invention, such as fruits, seeds, tubers, rootstocks, seedlings, cuttings etc.

It has been shown that protein expression in plants can be differentially enhanced in nectar by using a nectary-specific promoter, and that bees feeding on the nectar can pass the undigested protein into honey (New Scientist 26 Jun. 1999). Thus, the invention also extends to honey produced from plants expressing the growth hormone fragment of the invention.

Where the host cell is a microorganism, preferably the microorganism secretes the growth hormone fragment into the growth medium.

In one preferred embodiment, the host cell is a yeast, preferably a yeast of a genus such as *Saccharomyces, Pichia, Hansenula, Kluyveromyces* or the like, more preferably *Saccharomyces cereviseae* or *Pichia pastoris*. Where the yeast is *Saccharomyces cereviseae*, it may be of a strain suitable for production of beer, wine, or bread.

In a second preferred embodiment the host cell is a lactic acid bacterium or a probiotic organism. The lactic acid bacterium may be of the homolactic or heterolactic fermentation type.

In this embodiment the host cell is preferably selected from the group consisting of:

*Lactobacillus* species, such as *acidophilus, brevis, bulgaricus, buchneri, casei, confusus, cucumeris, curvatis, delbrueckii, farciminis, fermentum, fructivorans, helveticus, hilgardii, lactis, leichmanii, lotus, pasterianus, plantarum, reuteri, pentoaceticus, plantarum* and *sake;*

*Bifidobacterium* species, such as *bifidum, longum,* and *breve;*

*Leuconostoc* species, such as *cremoris, mesenteroides* and *mesenteroides* var. *sake;*

*Micrococcus* species;

*Pediococcus* species, such as *cerevisiae, halophilus, homari, pentosaceus* and *soyae;*

*Propionibacterium* species, such as *shermani;*

*Acetobacter* species, such as *rancens* and *xylium;*

*Bacillus* species, such as *brassicae fermentati, citreus, laterosporus, licheniformis, natto* and *pumillus;*

*Clostridium* species, such as *bifermentans;*

*Corynebacterium* species, such as *kusaya,*

*Halobacterium* species,

*Halococcus* species,

*Staphylococcus aureus* and *Staphylococcus epidermidis,* and

*Streptococcus* species, such as *cremoris, lactis, lactis* var. *diacetylactis, lactis* var. *hollandicus faecalis,* and *thermophilus.*

Even more preferably the host cell is selected from the group consisting of *Lactobacillus brevis, Lactobacillus bulgaricus, Lactobacillus buchneri, Lactobacillus casei, Lactobacillus farciminis, Lactobacillus fermentum, Lactobacillus fructivorans, Lactobacillus leichmanii, Lactobacillus pasteurianus, Lactobacillus plantarum, Propionibacterium shermani, Bifidobacterium bifidum, Bifidobacterium longum, Bifidobacterium breve,* and *Leuconostoc cremoris.*

The person skilled in the art will be aware that although some of these organisms, such as *Streptococcus faecalis, Staphylococcus aureus,* and *Staphylococcus epidermidis,* are pathogens in certain situations, these organisms do have strains which are used in the food industry.

In a third aspect, the invention provides a method of production of a fermented food or beverage product, comprising the step of using a starter culture of the invention. Preferably the food product is baked goods (if the growth hormone fragment is heat stable), cheese, yoghurt, a fermented food product, or a probiotic food. Preferably the beverage is a beer, a wine or a cider. However, the culture of the invention may also be added to products such as fruit juices or drinks, vegetable juices, or soft drinks.

In a fourth aspect, the invention provides a food or beverage product produced by or derived from a transformed cell or organism according to the invention. The nature of the food product will of course depend on the nature of the expression host.

It will be clearly understood that the invention also encompasses food or beverage products which are not themselves genetically modified, but which comprise a growth hormone fragment as defined above. Thus in a fifth aspect the invention provides a food, beverage or food additive comprising a growth hormone fragment which has the ability to modulate lipid metabolism.

In a sixth aspect, the invention provides a method selected from the group consisting of (a) controlling weight gain, (b) modifying fat/lean ratio, (c) modifying lipid metabolism, and (d) modifying food utilisation, comprising the step of administering a food or beverage product according to the invention as part of the diet of a mammal in need of such treatment. In one preferred embodiment, this aspect of the invention provides a method of improving the fat/lean ratio in domestic livestock raised for meat production.

It will be clearly understood that the method of the invention may be used in conjunction with one or more other such methods, including but not limited to dietary restriction or modification, exercise regimens, and administration of other modifiers of lipid metabolism.

The methods of the invention are applicable not only to humans, but also to domestic mammals such as cattle, sheep, pigs and horses, companion animals such as cats and dogs, and zoo animals including felids, canids, and non-human primates. In particular, it will be appreciated that in domestic animals used for meat production, control of food utilisation so as to maximise lean body mass is generally considered to be desirable.

While the invention is specifically described with reference to yeasts, it will be clearly understood that the method of the invention is applicable to a wide range of microorganisms, including organisms used in cheese, buttermilk and yoghurt starter cultures, organisms used in malolactic fermentation, and organisms used in the production of fermented food products such as soya sauce, kimchi, and sauerkraut.

For the purposes of this specification it will be clearly understood that the word "comprising" means "including but not limited to", and that the word "comprises" has a corresponding meaning.

The term "obesity" is to be understood to include both excess body weight and excess adipose tissue mass in the mammal, and therefore references to treatment of obesity include treatments designed to result in a reduction of body weight gain and/or reduction of adipose tissue mass of the obese mammal. Usually both a reduction of body weight gain and reduction of adipose tissue mass are desired. Thus the expected outcome of a treatment of obesity is reduction of overall body weight, and particular reduction of adipose tissue mass in the body. Adipose tissue mass is directly regulated by the processes of lipogenesis (fat production) and lipolysis (fat reduction). It is generally accepted that these biochemical processes are controlled by key metabolic enzymes. The key enzyme in lipogenesis is acetyl CoA carboxylase, and the key enzyme in lipolysis is hormone-sensitive lipase.

DETAILED DESCRIPTION OF THE INVENTION

The invention will now be described by way of reference only to the following non-limiting examples.

An amino acid sequence variant of the growth hormone fragment defined above is included within the scope of the invention, provided that it is functionally active. As used herein, the terms "functionally active" and "functional activity" in reference to the growth hormone fragment means that the growth hormone fragment is able to reduce body weight gain and adipose tissue mass following oral administration to a test mammal, such as a C57BL/6J (ob/ob) mouse or a Zucker fatty (fa/fa) rat. The C57 BL/6J (ob/ob) mouse and Zucker fatty (fa/fa) rat are well-recognized model systems for obesity in humans.

Amino acid sequence variants of the growth hormone fragment are prepared by introducing appropriate nucleotide changes into the growth hormone fragment DNA, and subsequently expressing the resulting modified DNA in a host cell, or alternatively may be prepared by in vitro synthesis. Such variants include deletions, insertions or substitutions of amino acid residues within the growth hormone fragment amino acid sequence set out above. Any combination of deletion, insertion, and substitution may be made to arrive at an amino acid sequence variant of the growth hormone fragment, provided that the variant possesses the desired functional characteristics described herein.

For example, due to the degeneracy of nucleotide coding sequences, mutations can be made in the growth hormone fragment nucleotide sequence without affecting the amino acid sequence of the growth hormone fragment encoded by this sequence. Other mutations can be made which will result in a growth hormone fragment which has an amino acid sequence different from that set out above, but which is functionally active. Such functionally active amino acid sequence variants of the growth hormone fragment are selected, for example, by substituting one or more amino acid residues in the amino acid sequence set out above with other amino acid residues of a similar or different polarity or charge.

One useful approach is called "alanine scanning mutagenesis." This method identifies an amino acid residue or group of target residues, for example charged residues such as arg, asp, his, lys, and glu, and, by means of recombinant DNA technology, replaces it with a neutral or negatively-charged amino acid, most preferably alanine or polyalanine, in order to modify the interaction of the amino acids with the surrounding aqueous environment in or outside the cell. See for example Cunningham et al., Science 244: 1081–1085 (1989). Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region, and the expressed growth hormone fragment variants are screened for functional activity.

Intrasequence insertions, i.e. insertions made within the amino acid sequence of the growth hormone fragment may range generally from about 1 to 10 residues, more preferably 1 to 5, most preferably 1 to 3 residues. Examples of terminal insertions include a growth hormone fragment with an N-terminal methionyl residue, such as may result from the direct expression of a growth hormone fragment in recombinant cell culture, and the growth hormone fragment with a heterologous N-terminal signal sequence to improve the secretion of the growth hormone fragment from recombinant host cells. Such signal sequences generally will be homologous to the host cell used for expression of the growth hormone fragment, and include STII or lpp for *E. coli*, alpha factor for yeast, and viral signals such as herpes gD for mammalian cells.

The third group of variants are those in which at least one amino acid residue in the amino acid sequence set out above, preferably one to four, more preferably one to three, even more preferably one to two, and most preferably only one, has been removed, and a different residue inserted in its place.

The sites of greatest interest for making substitutions are in the regions of the amino acid sequence set out above that have the greatest homology with other mammalian growth hormones. Such sites are likely to be important to the functional activity of the growth hormone fragment.

Accordingly, to retain functional activity, those sites, especially those falling within a sequence of at least three other identically conserved sites, are substituted in a relatively conservative manner. Such conservative substitutions are shown in Table 1 under the heading of preferred substitutions. If such substitutions do not result in a change in functional activity, then more substantial changes, denoted exemplary substitutions in Table 1, or as further described below in reference to amino acid classes, may be introduced, and the resulting variant growth hormone fragment analyzed for functional activity.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

The terms "cell," "host cell," "cell line," and "cell culture" are used interchangeably, and all such terms should be understood to include progeny of the cells. Thus the words "transformants" and "transformed cells" include the primary subject cell and cultures derived therefrom, without regard for the number of times the cultures have been passaged. It should also be understood that all progeny may not be precisely identical in DNA sequence, due to deliberate or inadvertent mutations.

"Plasmids" are DNA molecules that are capable of replicating within a host cell, either extrachromosomally or as part of the host cell chromosome(s), and are designated by a lower case "p" preceded and/or followed by capital letters and/or numbers. The starting plasmids herein are commercially available, are publicly available on an unrestricted basis, or can be constructed from such available plasmid, either as disclosed herein and/or in accordance with published procedures. In certain instances, as will be apparent to the person of ordinary skill in the art, other plasmids known in the art may be used interchangeably with plasmids described herein.

"Control sequences" refers to DNA sequences necessary for the expression of an operably linked nucleotide coding sequence in a particular host cell. Control sequences suitable for expression in prokaryotes include origins of replication, promoters, ribosome binding sites, and transcription termination sites. Control sequences suitable for expression in eukaryotes include origins of replication, promoters, ribosome binding sites, polyadenylation signals, and enhancers.

An "exogenous" element is one that is foreign to the host cell, or homologous to the host cell but in a position within the host cell in which the element is ordinarily not found.

"Digestion" of DNA refers to the catalytic cleavage of DNA with an enzyme which acts only at certain locations in the DNA. Such enzymes are called restriction enzymes or restriction endonucleases, and the sites within DNA where such enzymes cleave are called restriction sites. If there are multiple restriction sites within the DNA, digestion will produce two or more linearized DNA fragments (restriction fragments). The various restriction enzymes used herein are commercially available, and the appropriate reaction conditions, cofactors, and other requirements recommended by the manufacturers are used. Restriction enzymes are commonly designated by abbreviations composed of a capital letter followed by other letters representing the microorganism from which each restriction enzyme was originally obtained and a number designating the particular enzyme. In general, about 1 μg of DNA is digested with about 1–2 units of enzyme in about 20 μl of buffer solution. Appropriate buffers and substrate amounts for particular restriction enzymes are specified by the manufacturer, and/or are well known in the art.

"Recovery" or "isolation" of a given fragment of DNA from a restriction digest is typically accomplished by separating the digestion products, referred to as "restriction fragments," on a polyacrylamide or agarose gel by electrophoresis, identifying the fragment of interest on the basis of its mobility relative to that of marker DNA fragments of known molecular weight, excising the portion of the gel containing the desired fragment, and separating the DNA from the gel, for example by electroelution.

"Ligation" refers to the process of forming phosphodiester bonds between two double-stranded DNA fragments. Unless otherwise specified, ligation is accomplished using known buffers and conditions with 10 units of T4 DNA ligase per 0.5 μg of approximately equimolar amounts of the DNA fragments to be ligated.

"Oligonucleotides" are short-length, single- or double-stranded polydeoxynucleotides which are chemically synthesized by known methods, involving triester, phosphoramidite, or phosphonate chemistry, such as described by Engels et al., *Angew. Chem. Int. Ed. Engl.* 28:716–734 (1989). They are then purified, for example by polyacrylamide gel electrophoresis.

"Stringent conditions" for hybridization or annealing of nucleic acid molecules are those that (1) employ low ionic strength and high temperature for washing, for example 0.015 M NaCl/0.0015 M sodium citrate/0.1% sodium dodecyl sulfate (SDS) at 50° C., or (2) employ during hybridization a denaturing agent such as formamide, for example 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/mL), 0.1% SDS, and 10% dextran sulfate at 42° C., with washes at 42° C. in 0.2×SSC and 0.1% SDS.

"Growth hormone fragment nucleic acid" is RNA or DNA which encodes the growth hormone fragment. "Growth hormone fragment DNA" is DNA which encodes the growth hormone fragment. Another method for obtaining the growth hormone fragment nucleic acid is chemical synthesis, for example using one of the methods described by Engels, et al., *Angew. Chem. Int. Ed. Engl.* 28:716–734 (1989).

"Isolated" growth hormone fragment nucleic acid is growth hormone fragment nucleic acid which is identified and separated from, or otherwise substantially free from, contaminant nucleic acid encoding other polypeptides. The isolated growth hormone fragment nucleic acid can be incorporated into a plasmid or expression vector.

Isolated growth hormone fragment nucleic acid also is used to produce the growth hormone fragment by recombinant DNA and recombinant cell culture methods. In various embodiments of the invention, host cells are transformed or transfected with recombinant DNA molecules comprising an isolated growth hormone fragment DNA, to obtain expression of the growth hormone fragment DNA and thus the production of the growth hormone fragment in large quantities. DNA encoding amino acid sequence variants of the growth hormone fragment is prepared by a variety of methods known in the art. These methods include, but are not limited to, isolation from a natural source (in the case of naturally-occurring amino acid sequence variants of the growth hormone fragment) or preparation by site-directed (or oligonucleotide-mediated) mutagenesis, PCR mutagenesis, and cassette mutagenesis of an earlier prepared DNA encoding a variant or a non-variant form of the growth hormone fragment.

The growth hormone fragment DNA, whether cDNA or genomic DNA or a product of in vitro synthesis, is ligated into a replicable vector for further cloning or for expression. "Vectors" are plasmids and other DNAs that are capable of replicating autonomously within a host cell, and as such, are useful for performing two functions in conjunction with compatible host cells (a vector-host system). One function is to facilitate the cloning of the nucleic acid that encodes the growth hormone fragment, i.e., to produce usable quantities of the nucleic acid. The other function is to direct the expression of the growth hormone fragment. One or both of these functions are performed by the vector-host system. The vectors will contain different components, depending upon the function they are to perform as well as the host cell with which they are to be used for cloning or expression.

To produce the growth hormone fragment, an expression vector will contain nucleic acid that encodes the growth hormone fragment as described above. The growth hormone fragment of this invention is expressed directly in recombinant cell culture, or as a fusion with a heterologous polypeptide, preferably a signal sequence or other polypeptide having a specific cleavage site at the junction between the heterologous polypeptide and the growth hormone fragment. It will be clearly understood that the expression vectors and methods disclosed herein are suitable for use over a wide range of prokaryotic and eukaryotic organisms.

Prokaryotes may be used for the initial cloning of DNAs and the construction of the vectors useful in the invention. However, prokaryotes may also be used for expression of DNA encoding the growth hormone fragment *lactobacillus* is particularly contemplated. Plasmid or viral vectors containing replication origins and other control sequences derived from species compatible with the host cell are used in conjunction with prokaryotic host cells, for cloning or expression of an isolated DNA. For example, *E. coli* is typically transformed using pBR322, a plasmid derived from an *E. coli* species. See Bolivar, et al., *Gene* 2:95–113 (1987). PBR322 contains genes for ampicillin and tetracycline resistance, so that cells transformed by the plasmid can easily be identified or selected. Alternative selection or identification markers, such as sequences encoding epitope tags or a fluorescent marker such as green fluorescent protein or luciferase, may also be used. To serve as an expression vector, the pBR322 plasmid, or other plasmid or viral vector, must also contain, or be modified to contain, a promoter that functions in the host cell to provide messenger RNA (mRNA) transcripts of a DNA inserted downstream of the promoter. See Rangagwala et al., *Bio/Technology* 9:477–479 (1991).

In addition to prokaryotes, eukaryotic microbes, such as yeast, may also be used as hosts for the cloning or expression of DNAs useful in the invention. *Saccharomyces cerevisiae*, or common baker's yeast, is the most commonly used eukaryotic microorganism. *Pichia pastoris* is also widely used. Plasmids useful for cloning or expression in yeast cells of a desired DNA are well known, as are various promoters that function in yeast cells to produce mRNA transcripts.

Furthermore, cells derived from multicellular organisms also may be used as hosts for the cloning or expression of DNAs useful in the invention. Transgenic plants are particularly contemplated. Expression vectors, unlike cloning vectors, should contain a promoter which is recognized by the host organism and is operably linked to the growth hormone fragment nucleic acid. Promoters are untranslated sequences that are located upstream from the start codon of a gene and that control transcription of the gene, i.e the synthesis of mRNA. Promoters typically fall into two classes, inducible and constitutive. Inducible promoters are promoters that initiate high level transcription of the DNA under their control in response to some change in culture conditions, for example the presence or absence of a nutrient or a change in temperature.

A large number of promoters are known, and these may be operably linked to the growth hormone fragment DNA to achieve expression of the growth hormone fragment in a host cell. Although the promoter associated with naturally-occurring growth hormone DNA is usable, heterologous promoters will generally result in greater transcription and higher yields of expressed growth hormone fragment.

Promoters suitable for use with prokaryotic hosts include the β-lactamase and lactose promoters; see Goeddel, et al., *Nature* 281:544–548 (1979), tryptophan (trp) promoter, Goeddel, et al., *Nuc. Acids Res.* 8:4057–4074 (1980), and hybrid promoters such as the tac promoter; see deBoer, et al., *Proc. Natl. Acad. Sci. USA* 80:21–25 (1983). However, other known bacterial promoters are suitable. Their nucleotide sequences have been published (Siebenlist, et al., *Cell* 20:269–281 (1980)), thereby enabling a skilled worker operably to ligate them to DNA encoding the growth hormone fragment using linkers or adaptors to supply any required restriction sites (Wu, et al., *Meth. Enz.* 152:343–349 (1987)).

Suitable promoters for use with yeast hosts include the promoters for 3-phosphoglycerate kinase (Hitzeman, et al., *J. Biol. Chem.* 255:12073–12080 (1980); Kingsman, et al., *Meth. Enz.* 185:329–341 (1990)), or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase (Dodson, et al., *Nuc. Acids res.* 10:2625–2637 (1982); Emr, *Meth. Enz.* 185:231–279 (1990)).

Furthermore, it is also possible, and often desirable, to utilize promoter or other control sequences associated with a naturally-occurring DNA which encodes the growth hormone fragment, provided that such control sequences are functional in the particular host cell used for recombinant DNA expression.

Other control sequences desirable in an expression vector in addition to a promoter are a ribosome binding site, and, in the case of an expression vector used with eukaryotic host cells, an enhancer. Enhancers are cis-acting elements of DNA, usually about from 10–300 bp, which act on a promoter to increase the level of transcription. Many enhancer sequences from mammalian genes are now known, for example those from the genes for globin, elastase, albumin, α-fetoprotein and insulin. Typically, however, the enhancer used will be one from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See Kriegler, Meth. Enz. 185:512–527 (1990).

Expression vectors may also contain sequences necessary for the termination of transcription and for stabilizing the mRNA; see Balbas, et al., *Meth. Enz.* 185:14–37 (1990); Levinson, *Meth. Enz.* 185:485–511 (1990). In the case of expression vectors used with eukaryotic host cells, such transcription termination sequences may be obtained from the untranslated regions of eukaryotic or viral DNAs or cDNAs. These regions contain polyadenylation sites as well as transcription termination sites. See Birnsteil, et al., *Cell* 41:349–359 (1985).

In general, control sequences are DNA sequences necessary for the expression of an operably-linked coding sequence in a particular host cell. "Expression" refers to transcription and/or translation. "Operably-linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

Expression and cloning vectors will also contain a sequence which enables the vector to replicate in one or more selected host cells. Generally, in cloning vectors this sequence is one that enables the vector to replicate independently of the host chromosome(s), and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins, for example those from SV40, polyoma, or adenovirus, are useful for cloning vectors in mammalian cells. Most expression vectors are "shuttle" vectors, i.e. they are capable of replication in at least one class of organisms but can be transfected into another organism for expression. For example, a vector may be cloned in *E. coli*, and then the same vector is transfected into yeast or plant cells for expression, even though it is not capable of replicating independently of the host cell chromosome.

Many selectable markers which may be used for identifying and isolating recombinant host cells that express the growth hormone fragment are known. For example, a suitable selection marker for use in yeast is the trp1 gene present in the yeast plasmid YRp7. See Stinchcomb, et al., *Nature* 282:39–43 (1979); Kingsman, et al., *Gene* 7:141–152 (1979); Tschemper, et al., *Gene* 10:157–166 (1980). The trp1 gene provides a selection marker for a mutant strain of yeast lacking the ability to grow in tryptophan, for example, ATCC No. 44076 or PEP4-1 (available from the American Type Culture Collection, Rockville, Md. 20852 USA). See Jones, *Genetics* 85:12 (1977). The presence of the trp1 lesion in the yeast host cell genome then provides an effective environment for detecting transformation by growth in the absence of tryptophan. Similarly, Leu2-deficient yeast strains (ATCC Nos. 20622 or 38626) are complemented by known plasmids bearing the Leu2 gene.

Since it is may be difficult to predict in advance the characteristics of an amino acid sequence variant of the growth hormone fragment, it will be appreciated that some screening of such variants will be needed to identify those that are functionally active. Such screening may be performed in vitro, for example using routine assays for the effect of the fragment on lipogenesis by isolated adipose tissue of C57Bl (Ob/Ob) mice.

As used herein, the terms "transformation" and "transfection" refer to the process of introducing a desired nucleic acid, such a plasmid or an expression vector, into a host cell. Various methods of transformation and transfection are available, depending on the nature of the host cell. In the case of *E. coli* cells, the most common methods involve treating the cells with aqueous solutions of calcium chloride and other salts. In the case of mammalian cells, the most common methods are transfection mediated by either calcium phosphate or DEAE-dextran, or electroporation. See Sambrook, et al., eds., *Molecular Cloning*, pp. 1.74–1.84 and 16.30–16.55 (Cold Spring Harbor Laboratory Press, 1989). Following transformation or transfection, the desired nucleic acid may integrate into the host cell genome, or may exist as an extrachromosomal element.

Host cells transformed or transfected with the above-described plasmids and expression vectors are cultured in conventional nutrient medium modified as is appropriate for inducing promoters or selecting for drug resistance or some other selectable marker or phenotype. The culture conditions, such as temperature, pH, and the like, suitably are those previously used for culturing the host cell used for cloning or expression, as the case may be, and will be apparent those skilled in the art.

In addition to prokaryotes, eukaryotic microbes such as yeast are suitable hosts for the growth hormone fragment-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; see Beach and Nurse, *Nature* 290:140–142 (1981), and *Pichia pastoris*, Cregg, et al., *Bio/Technology* 5:479–485 (1987); Sreekrishna, et al., *Biochemistry* 28:4117–4125 (1989), *Neurospora crassa*, Case, et al., *Proc. Natl. Acad. Sci. USA* 76:5259–5263 (1979).

Suitable host cells for the expression of the growth hormone fragment also include those derived from multicellular organisms. Such host cells are capable of complex processing and glycosylation activities. In principle, any higher eukaryotic cell culture, whether from vertebrate or invertebrate culture, is useable. Examples of invertebrate cells include plant cells. Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously altered to contain the growth hormone fragment DNA. During incubation of the plant cells with *A. tumefaciens*, the DNA encoding the growth hormone fragment is transferred into cells, so that they become transfected, and will, under appropriate conditions, express the growth hormone fragment DNA. In addition, regulatory and signal sequences compatible with plant cells are available, such as the nopaline synthase promoter and polyadenylation signal sequences, and the ribulose biphosphate-carboxylase promoter. See Depicker, et al., J. Mol. Appl. Gen. 1:561–573 (1982). Herrera-Estrella, et al., Nature 310:115–120 (1984). In addition, DNA segments isolated from the upstream region of the T-DNA 780 gene are capable of activating or increasing transcription levels of plant-expressible genes in recombinant DNA-containing plant tissue. (European Pat. Pub. No. EP 321,196 (published Jun. 21, 1989)). Methods of regenerating whole plants from tissue culture are well known and routine in the art.

In order to express the nucleic acid molecule of the invention in plant cells, the nucleic acid is linked to regulatory DNA elements which ensure their transcription in plant cells. Such regulatory DNA elements are preferably promoters. In principle any promoter which is active in plant cells may be used. The promoter may be selected so that the expression takes place constitutively or only in a certain tissue, at a certain point of time of the plant development or at a point of time determined by external factors. The promoter may be homologous or heterologous with respect to the plant. Suitable promoters for constitutive expression include the $^{35}$S RNA promoter of the Cauliflower Mosaic Virus and the ubiquitin promoter from maize. For tuber-specific expression in potatoes the patatin gene promoter B33 (Rocha-Sosa et al., EMBO J. 8 (1989), 23–29) may be used. Alternatively a promoter which ensures expression only in photosynthetically active tissues can be used, e.g. the ST-LS1 promoter (Stockhaus et al., Proc. Natl. Acad. Sci. USA 84 (1987), 7943–7947; Stockhaus et al., EMBO J. 8 (1989), 2445–2451). For endosperm-specific expression the HMG promoter from wheat, the USP promoter, the phaseolin promoter or promoters from zein genes from maize are suitable.

Furthermore, a termination sequence may be present, in order to end the transcription correctly and to add a poly-A-tail to the transcript; this is believed to stabilize the transcripts. Such elements are described in the literature (cf. Gielen et al., EMBO J. 8 (1989), 23–29), and can be exchanged as desired.

A large number of cloning vectors are available for the introduction of foreign genes into higher plants; these usually contain a replication signal for *E. coli* and a marker gene for the selection of transformed bacterial cells. Examples of such vectors are pBR322, pUC series, the M13 mp series, pACYC184 etc. The desired sequence may be integrated into the vector at a suitable restriction site. The obtained plasmid is used for the transformation of *E. coli* cells. Transformed *E. coli* cells are cultivated in a suitable medium and subsequently harvested and lysed. The plasmid is recovered, and its DNA characterized by restriction analysis, gel electrophoresis and other biochemical or molecular biological methods. After each manipulation the plasmid DNA may be cleaved and the obtained DNA fragments may be linked to other DNA sequences. Each plasmid DNA may be cloned into the same or other plasmids.

A wide range of techniques for introducing DNA into a plant host cell are available. These techniques include the transformation of plant cells with T-DNA by using *Agrobacterium tumefaciens* or *Agrobacterium rhizogenes* as transformation medium, the fusion of protoplasts, injection or electroporation of DNA, and the introduction of DNA by the biolistic method.

For injection and electroporation of DNA into plant cells, there are no special requirements for the plasmids, and simple plasmids such as pUC derivatives may be used. However, if whole plants are to be regenerated from cells transformed in this way, a selectable marker gene should be present.

Depending on the method of introducing the nucleic acid molecule into the plant cell, further DNA sequences may be necessary. If the Ti- or Ri-plasmid is used, e.g. for the transformation of the plant cell, at least the right border, and preferably both the right and left border, of the Ti- and Ri-plasmid T-DNA should be operably linked as a flanking region to the nucleic acid to be introduced.

If *Agrobacterium* is used for the transformation, the DNA which is to be integrated must be cloned either into an intermediate vector or into a binary vector. Because of the presence of sequences homologous to the sequences within the T-DNA, the intermediate vectors may be integrated into the Ti- or Ri-plasmid of the *Agrobacterium* by homologous recombination. The intermediate vector also contains the vir-region necessary for the transfer of the T-DNA. Intermediate vectors cannot replicate in *Agrobacterium*. The intermediate vector may be transferred to *Agrobacterium tumefaciens* by conjugation using a helper plasmid. Binary vectors replicate in another species such as *E. coli* as well as in *Agrobacterium*. They contain a selectable marker gene, as well as a linker or polylinker which is framed by the right and the left T-DNA border region. They may be transformed directly into the *Agrobacterium* (Holsters et al. Mol. Gen. Genet. 163 (1978), 181–187). The *Agrobacterium* host cell should contain a plasmid carrying a vir-region. The vir-region is necessary for the transfer of the T-DNA into the plant cell. Additional T-DNA may be present. *Agrobacterium* transformed in such a way is used for the transformation of plant cells.

The use of T-DNA for the transformation of plant cells was investigated extensively and described in detail in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

For transferring the DNA into the plant cells, plant explants may suitably be co-cultivated with *Agrobacterium tumefaciens* or *Agrobacterium rhizogenes*. From the infected plant material, e.g. pieces of leaves, stem segments, roots, or protoplasts or suspension-cultivated plant cells, whole plants may then be regenerated in a suitable medium which may contain antibiotics or biocides for the selection of transformed cells. The plants obtained in such a way may then be examined as to whether the introduced DNA is present or not. Other methods for introducing foreign DNA by the biolistic method or by transforming protoplasts are known to the skilled person; see for example Willmitzer, L., 1993 Transgenic plants. In: Biotechnology, A Multi-Volume Comprehensive Treatise (H. J. Rehm, G. Reed, A. Pühler, P. Stadler, editors), Vol. 2, 627–659, VCH Weinheim-New York-Basel-Cambridge).

Although the transformation of dicotyledonous plants via Ti-plasmid vector systems by means of *Agrobacterium tumefaciens* is well established, more recent studies indicate that monocotyledonous plants are also suitable for transformation using vectors based on *Agrobacterium* (Chan et al., Plant Mol. Biol. 22 (1993), 491–506; Hiei et al., Plant J. 6 (1994), 271–282). Alternative systems for the transformation of monocotyledonous plants include transformation by means of a biolistic gun, protoplast transformation, the electroporation of partially permeabilized cells, and introduction of DNA by means of glass fibres.

There are various references in the relevant literature dealing specifically with the transformation of maize; see for example WO95/06128, EP 0 513 849, and EP 0 465 875. In EP 292 435 a method is described by means of which fertile plants may be obtained starting from mucousless, friable granulous maize callus. In this context it was observed by Shillito et al. (Bio/Technology 7 (1989), 581) that for regenerating fertile plants it is necessary to start from callus-suspension cultures from which a culture of dividing protoplasts can be produced which is capable to regenerate to plants. After an in vitro cultivation period of 7 to 8 months Shillito et al. obtained plants with viable descendants; however, these exhibited abnormalities in morphology and reproductivity. Prioli and Söndahl (Bio/Technology 7 (1989), 589) have described how to regenerate and to obtain fertile plants from maize protoplasts of the Cateto maize inbred line Cat 100-1. The authors suggest that the regeneration of protoplasst to fertile plants depends on a number of factors such as the genotype, the physiological state of the donor cell, and the cultivation conditions.

Once the introduced DNA has been integrated into the genome of the plant cell, it usually remains stable, and also remains within the descendants of the originally transformed cell. It may contain a selectable marker which confers resistance against biocides or against an antibiotic such as kanamycin, G 418, bleomycin, hygromycin or phosphinothricin on the transformed plant cells. The individually selected marker permits selection of transformed cells against cells lacking the introduced DNA.

The transformed cells grow in the usual way within the plant (see also McCormick et al., Plant Cell Reports 5 (1986), 81–84). The resulting plants can be cultivated in the usual way and cross-bred with plants having the same transformed genotype or another genotype. The resulting hybrid individuals have the corresponding phenotypic properties.

Two or more generations should be grown in order to ensure that the phenotypic feature is stable and that it is transferred. Furthermore, seeds should be harvested in order to ensure that the corresponding phenotype or other properties is retained.

Construction of suitable vectors containing the nucleotide sequence encoding the growth hormone fragment and appropriate control sequences employs standard recombinant DNA methods. DNA is cleaved into fragments, tailored, and ligated together in the form desired to generate the vectors required.

For analysis to confirm correct sequences in the vectors constructed, the vectors are analyzed by restriction digestion to confirm the presence in the vector of predicted restriction endonuclease cleavage sites, and/or by sequencing by the dideoxy chain termination method of Sanger, et al., *Proc. Nat. Acad. Sci. USA* 72:3918–3921 (1979).

It is further contemplated that the growth hormone fragment of this invention may be produced by homologous recombination, for example, as described in PCT Patent Publication No. WO 91/06667 (published May 16, 1991). Briefly, this method involves transforming cells containing an endogenous gene encoding the growth hormone fragment with a homologous DNA, which comprises an amplifiable gene, such as DHFR, and at least one flanking sequence, having a length of at least about 150 base pairs, which is homologous with a nucleotide sequence in the cell genome that is within or in proximity to the gene encoding the growth hormone fragment. The transformation is carried out under conditions such that the homologous DNA integrates into the cell genome by recombination. Cells having integrated the homologous DNA are then subjected to conditions which select for amplification of the amplifiable gene, whereby the growth hormone fragment gene is amplified concomitantly. The resulting cells then are screened for production of desired amounts of the growth hormone fragment. Flanking sequences which are in proximity to a gene encoding the growth hormone fragment are readily identified, for example, by the method of genomic walking, using as a starting point the growth hormone fragment nucleotide sequence set out above (Spoerel, et al., Meth. Enz. 152:598–603 (1987)).

Gene amplification and/or gene expression may be measured in a sample directly, for example, by conventional Southern blotting to quantitate DNA, or by Northern blotting to quantitate mRNA, using an appropriately labeled oligonucleotide hybridization probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radioisotopes, fluorophores, chromophores, or the like. Alternatively, antibodies which can recognize specific duplexes, including DNA duplexes, RNA duplexes, and DNA-RNA hybrid duplexes or DNA-protein duplexes, may be employed. The antibodies in turn may be labelled, and the assay may include a step in which the duplex is bound to a surface, so that upon the formation of duplex on the surface, the presence of antibody bound to the duplex can be detected. Gene expression may alternatively be measured by immunological methods, such as immunohistochemical staining of tissue sections and assay of cell culture or body fluids, to quantitate directly the expression of the gene product, the growth hormone fragment. With immunohistochemical staining techniques, a cell sample is prepared, typically by dehydration and fixation, followed by reaction with labelled antibodies specific for the gene product coupled, where the labels are usually visually detectable, such as enzymatic labels, fluorescent labels, luminescent labels, and the like. A particularly sensitive staining technique suitable for use in the present invention is described by Hsu, et al., *Am. J. Clin. Path.*, 75:734–738 (1980).

The food or beverage comprising the growth hormone fragment is optionally combined with or administered in concert with one or more other agents to achieve a desired therapeutic effect. For example, the growth hormone fragment may be used together with another modifier of lipid metabolism to achieve a synergistic effect on lipogenesis in adipose tissue, wherein the term "synergistic" means that the effect of the combination of the growth hormone fragment with a second substance is greater than that achieved with either substance used individually.

An effective amount of the growth hormone fragment to be employed therapeutically will depend, for example, upon the therapeutic objectives, the route of administration, and the condition of the subject. Accordingly, it will be necessary for the therapist to titrate the dosage and modify the route of administration as required to obtain the optimal therapeutic effect. A typical daily dosage might range from about 1 μg/kg to up to 100 mg/kg or more, depending on the factors mentioned above.

Fermented food products include beer, wine, bread, cheese, and yoghurt. Beer, wine, and bread production primarily uses yeasts, the most common of which is *Saccharomyces cereviseae*. The production of certain types of bread, usually known as sour-dough breads, fermented meat products such as salami, fermented vegetable products and pulses, and milk products such as buttermilk, cheese and yoghurt, utilises bacterial starter cultures, which are most commonly members of the genus *Lactobacillus*. Organisms of the genus *Leuconostoc* are used in the production of foods such as sauerkraut, and in butter manufacture. In addition to this, certain wine styles are produced using malolactic fermentation, which also requires bacterial starter cultures, usually of the genera *Lactobacillus, Leuconostoc* or *Pediococcus*.

Although fermented foods have been used in a number of different human societies for many centuries, more recently it has been recognised that some of these foods, especially fermented milk products such as yoghurts, contain bacteria which are the same as or closely related to some of the bacteria which are normally present in the intestine and female genital tract, and that for this reason they are particularly easy to digest, and can even have a beneficial effect if the normal intestinal flora has been disrupted, for example because of antibiotic treatment for a medical condition. The bacteria present in these products are known as probiotic organisms, and foods containing them are referred to as probiotic foods. Such products are becoming increasingly popular, and for example the fermented milk product marketed under the name Yakult (Trade mark) is enormously popular in Japan, and has an increasing market in Australia.

The baking industry uses large quantities of defined yeast cultures to produce modern sour-dough breads and baked goods. Sour-dough bakery products are becoming increasingly popular as they stay soft longer, with less mould growth, than yeast-only breads. They are widely believed to be healthier, being more easily digested, and are regarded as being less likely to elicit allergies, and as being able to provide more vitamins, amino acids, and fatty acids than conventional bakery products. Examples of sour dough products include:

San Francisco-type sour-dough breads which are well known in San Francisco, U.S.A.; the organism used in production of this unique bread is *Lactobacillus sanfrancisco*.

Panettone, Colombie, Pandoro, and various other small cakes and sweet baked goods widely produced in Italy.

Sour rye breads and baked goods such as pumpernickel, widely used in Germany, Scandinavia and other parts of northern Europe.

Shamsy and Kisra breads of the Middle East.

Idli and Puto breads of the South Pacific and Asian region.

Soda crackers, widely produced in the United States and Australia.

Materials and Methods

C57B1/6J (Ob/Ob) mice, assessment of cumulative weight gain and food consumption, determination of adipose tissue weight, and assays of plasma triglyceride, total cholesterol, and tissue lipogenic activity were all as described in Australian Patent No. 693478 (U.S. Pat. No. 5,869,452).

EXAMPLE

Expression of AOD 9604 in Yeast

Peptides comprising the human growth hormone fragment analog AOD9604, corresponding to Tyr-hGH 177–191 were produced by expression of the recombinant peptide in yeast. The amino acid sequence, expressed in the standard single letter amino acid cod, of AOD9604 is $NH_2$-YL-RIVQCRSVEGSCGF-COOH (SEQ ID NO: 9), and the active peptide is thought to be the circular form which results from intramolecular disulphide bonding between the two cysteine residues.

Oligonucleotides coding for this peptide sequence were designed, using codons which are highly biased for expression in bakers/brewers yeast (*Saccharomyces cerevisiae*). A methionine codon (ATG) was included in the preliminary constructs in order to allow the synthesis of a limited range of oligonucleotides which were most readily compatible with as many different expression vectors as possible. The oligonucleotides selected were also compatible with two of the vectors for in-frame translation, with various signals for secretion, and with the YEpFlag 1 vector for in-frame fusion to the epitope sequence FLAG, which has the amino acid sequence DYKDDDK (SEQ ID NO: 10), and which can be detected using a commercially-available monoclonal antibody (for example, anti-Flag M2 antibody, IBI, New Haven, Conn.).

Incorporation of an epitope tag was used in order to enable preliminary screening to determine whether the peptide was expressed in yeast, as initially it was not certain that the peptide would be synthesised or be detectable using polyclonal rabbit antibodies which recognise AOD9604. Thus it was necessary to confirm that the peptide was expressed in yeast and to test whether there was any deleterious effect on the yeast host.

The following pairs of oligonucleotides were synthesised:

1. For cloning into the EcoRI-NotI sites of YEpFlag and pPIC9K to produce a fusion protein for secretion into the culture medium, using either the ethanol-induced ADH2 promoter in YEpFlag 1 or the methanol induced AOX1 promoter in pPIC9K:

KH-Pr-1U

EcoRI Forward-5'-AA TTC ATG TAC TTC AGA ATT GTT CAA TGT AGA TCC GTT GAA GGT TCT TGT GGT TTC TAA CG-3' (SEQ ID NO 1)

KH-Pr-1D

NotI-Reverse 5'-GGCCGC TTA GAA ACC ACA AGA ACC TTC AAC AGG TCT ACA TTG AAC AAT TCT GAA GTA CAT G-3' (SEQ ID NO 2)

2. For cloning into the EcoRI-BamHI sites of YEpFlag and pYEULC-E to produce a either a fusion protein tagged with FLAG and induced by ethanol induction from the ADH2 promoter, or a protein produced intracellularly following copper induction from the CUP1 promoter:

KH-Pr-2U

EcoRI-Up 5'-AA TTC ATG TAC TTC AGA ATT GTT CAA TGT AGA TCC GTT GAA GGT TCT TGT GGT TTC TAA G-3' (SEQ ID NO 3)

KH-Pr-2D

BamHI-Down 5'-GATC C TTA GAA ACC ACA AGA ACC TTC AAC AGG TCT ACA TTG AAC AAT TCT GAA GTA CAT G-3' (SEQ ID NO 4)

3. For cloning into the BamHI-EcoRI sites of pYEULC-BX, which would be expected to result in intracellular production of the protein following induction by copper, and to requiring the presence of an ATG initation codon:

KH-Pr-3U

BamHI-FRONT 5'-GATC C ATG TAC TTC AGA ATT GTT CAA TGT AGA TCC GTT GAA GGT TCT TGT GGT TTC TAA G-3' (SEQ ID NO 5)

KH-Pr-3D

EcoRI-BACK 5'-AATT C TTA GAA ACC ACA AGA ACC TTC AAC AGG TCT ACA TTG AAC AAT TCT GAA GTA CAT G-3' (SEQ ID NO 6)

4. For cloning into the pYX series of vectors, in order to assess whether a differently induced promoter, such as the galactose-inducible GAL promoter, the glucose-inducible TPI promoter or the constitutively-expressed 786 weak promoter, might result in better expression in the event that high level expression produced deleterious effects on the yeast host. These vectors rely on the ATG methionine initiation codon for translation of the peptide, and would produce intracellular unfused protein.

KH-Pr-4U pYX-EcoRI-ON 5'-AA TTC ATG TAC TTC AGA ATT GTT CAA TGT AGA TCC GTT GAA GGT TCT TGT GGT TTC TAA G-3' (SEQ ID NO 7)

KH-Pr4D pYX-Sal I-OFF 5'-TCGA C TTA GAA ACC ACA AGA ACC TTC AAC AGG TCT ACA TTG AAC AAT TCT GAA GTA CAT G-3' (SEQ ID NO 8)

All the sequences include an ATG initiating codon, which is not expected to effect the activity of the peptide; in any event the resultant N-terminal methionine residue can be readily cleaved from Tyrosine 1 of AOD9604 by cyanogen bromide (CNBr) treatment. This also allows for removal of the Flag tag, which may alternatively be removed by enterokinase treatment. Similarly the fusion of CUP1 to AOD9604 in the pYEULC-E constructs can also be removed by CNBr treatment. Alternatively the construct can omit the ATG codon.

This construct was made because we have previously found that the addition of a few yeast amino acids, encoded by a native yeast gene, to the $NH_2$-terminus of a recombinant product can have a protective effect and increase yields. The single methionine may also have a protective effect for the peptide, as some amino acids at the $NH_2$ terminus actually promote degradation via the ubiquitin pathway. By producing a variety of constructs for expression it was hoped that most eventualities could be covered. The codons were selected so as to favour high expression in yeast. However, the optimum yeast codon TCT, which results in an internal BglII site, was changed to the codon TCC, which is the next-most commonly used in yeast, as we wished to use the BglII site for subsequent subcloning into expression vectors for *Pichia pastoris*.

The oligonucleotide pairs were checked as follows to ensure that the sequence overlaps were correct:

```
KH-1  5'-AA TTC ATG TAC TTC AGA ATT GTT CAA TGT AGA
         TCC GTT GAA GGT TCT TGT GGT TTC TAA GC-
         3' (SEQ ID NO:18)

G TAC ATG AAG TCT TAA CAA GTT ACA TCT AGG
         CAA CTT CCA AGA ACA CCA AAG ATT CGCCGG-
         5' (SEQ ID NO:11)
```

```
KH-2  5'-AA TTC ATG TAC TTC AGA ATT GTT CAA TGT
         AGA TCC GTT GAA GGT TCT TGT GGT TTC TAA G-
         3' (SEQ ID NO:12)

G TAC ATG AAG TCT TAA CAA GTT ACA TCT AGG CAA
         CTT CCA AGA ACA CCA AAG ATT C CTAG-
         5' (SEQ ID NO:13)

KH-3  5-GATC C ATG TAC TTC AGA ATT GTT CAA TGT AGA
        TCC GTT GAA GGT TCT TGT GGT TTC TAA G-
        3' (SEQ ID NO:14)

G TAC ATG AAG TCT TAA CAA GTT ACA TCT AGG CAA
        CTT CCA AGA ACA CCA AAG ATT C TTAA-
        5' (SEQ ID NO:15)

KH-4  AA TTC ATG TAC TTC AGA ATT GTT CAA TGT AGA
      TCC GTT GAA GGT TCT TGT GGT TTC TAA G-
      3' (SEQ ID NO:16)

G TAC ATG AAG TCT TAA CAA GTT ACA TCT AGG CAA
      CTT CCA AGA ACA CCA AAG ATT C AGCT-
      5' (SEQ ID NO:17)
```

The recombinant expression constructs were made using standard methods, as described in the standard textbook by Sambrook et al 1989. Oligonucleotides were mixed in equal ratios according to the pairs described above, heated to 100° C., and cooled slowly at room temperature to allow annealing. Appropriate pairs were mixed at ratios of 3 mole oligonucleotide to 1 mole vector, cleaved with appropriate restriction enzymes, and purified by agarose gel electrophoresis. Ligation was performed overnight at 16° C., and aliquots of ligation mix used to transform XL1-Blue electrocompetent *E. coli*. Ampicillin-resistant transformants were obtained by culture of electroporated *E. coli* on ampicillin selection plates.

Transformants were screened by hybridisation with $^{32}P$ oligonucleotides 5'-end labelled by polynucleotide kinase. Plasmid DNA was isolated from transformants identified as positive by autoradiography, and subjected to restriction enzyme analysis and electrophoresis on agarose gels. The presence of the desired cloned oligonucleotides was confirmed by Southern transfer and rehybridisation with labelled oligonucleotide probes.

The following constructs were cloned into the yeast vectors YEpFlag1-, pYEULC-BX, pYEULC-S and pYEULC:

YEpFlag-AOD-9604
pYEULC-BX-AOD 9604
pYEULC-E-AOD 9604
pYEULC-S-AOD 9604

All these yeast vectors are shuttle vectors designed for use with the yeast *S. cerevisiae*; they have a bacterial origin of replication, and comprise the ampicillin resistance gene Amp as a selectable marker. This allows the initial cloning to be performed in the bacterium *E. coli*, which is more easily manipulated. All the vectors have a 2v native yeast plasmid origin of replication (ori) for multicopy high number replication in yeast. Individual vectors have the following specific features:

1. YEpFlag1: TRP1 selection in yeast, expression induced by ethanol through the ADH2 promoter, alpha factor pre-pro signal sequence for secretion and folding, Flag epitope tag for detection (Vaughan et al 1998);

2. pYEULC-BX: requires a methionine codon for initiation of translation and internal production;

3. pYEULC-S: produces a secreted product through the killer toxin secretion signal, with the product cleaved from the fusion to produce Met-AOD-9604; and 4. pYEULC-E: translation from the native CUP1 metallothionein gene produces an intracellular fusion product of the form MFSEF-M-AOD-9604.

The members of the pYEULC series of vectors all have the selectable markers URA3, LEU2-d, and copper induction of expression via the CUP1 promoter (Macreadie et al 1992; Macreadie and Vaughan 1998).

The oligonucleotides can also be cloned into pPIC9K and various members of the pYX series of vectors, using the EcoRI-NotI sites, for expression in *Pichia pastoris*.

Sequencing across cloning sites in both directions showed that all the constructs had the expected nucleotide sequence and reading frame. All the constructs were introduced into the yeast strains BJ3505 [α ura3-52 trp1-101 lys2-208 gal2can1 pepp4:: HIS3 prb1-6R] or BJ5462 [α ura3–52 trp1 leu2-1 his3-200 can1 GAL pep4:: HIS3 prb1-6R] by electroporation. These strains are protease deficient and non-reverting for selectable markers. TRP$^+$ transformants were obtained for YEpFlag constructs, and URA$^+$ or LEU$^+$ or URA$^+$ and LEU$^+$ transformants were obtained for all the pYEULC-based vectors. Selection pressure was maintained on SD plates lacking trp, ura or leu, but not on medium lacking both amino ura and leu, as this caused too much nutrient stress for transformants to grow strongly in liquid culture.

Expression was initially assessed by colony hybridisation on nitrocellulose filters, using detection with M2 [anti-Flag] or polyclonal anti-AOD 9604 antibody. Trial fermentations were also monitored for expression following induction, either by ethanol for the YepFlag-based construct or by copper for the pYEULC-based constructs, by slot blotting supernatants and pellets, and hybridising with antibodies as previously described. Western blots with anti-Flag M2 produced strong signals for YEpFlag-AOD-9604 in both strains, while all transformants produced a weak signal with rabbit polyclonal anti-AOD9604, although the signal was of similar strength to that observed with purified peptide, which was used as a standard. Proteins were also transferred to nitrocellulose and stained with amido black; these showed bands of the expected size, ie similar to that of the standard peptide. Estimates of concentration were made using a standard curve obtained using serial dilutions of synthetic peptide. The YEpFlag material was also shown to have a free NH$_2$ terminal end, as shown by its ability to bind anti-Flag M1, which binds only to Flag in which the NH$_2$ terminal is free.

For production of recombinant product for functional analysis, recombinant yeast samples were cultured in SD selective medium (0.67% yeast nitrogen base (Difco), 2% glucose), and 500 ml lots were then grown in various media (YEPD (1% yeast extract, 2% BActo peptone, 2% glucose), YEPGalactose, YEPM, YPHSM and SD) and in the presence of various concentrations of copper (500 μM, 750 μM or 1000 μM). The production of the peptide was monitored by antibody titration at different time points.

Freeze-dried material was produced from 300 ml of culture supernatant, from which yeast transformants were separated by centrifugation at 10K rpm in a JA10 rotor in an Avanti J25 centrifuge. Following centrifugation, supernatants were decanted into Schott bottles and stored frozen at −20° C., or freeze-dried and then stored at −20° C.

The following samples were subjected to testing for hypoglycaemic effect:

1. Supernatant (concentrated by freeze-drying) of YEpFlag-AOD-9604 in YEPD medium (in the form of DYKDDDDK-EF-M-AOD-9604 (SEQ ID NO: 19));

2. Supernatant (non-concentrated) of YEpFlag-AOD-9604 in YEPD medium;

3. Supernatant (non-concentrated) of YEpFlag-AOD-9604 in SD medium;

4. Supernatant (concentrated by freeze-drying) of pYEULC-S-AOD-9604 in YEPD medium (in the form of M-AOD-9604);

5. Supernatants (concentrated by freeze-drying) of pYEULC-S-AOD-9604 in SD medium;

6. Supernatant (non-concentrated) of pYEULC-S-AOD-9604 in YEPD medium (in the form of M-AOD-9604);

7. Supernatant (non-concentrated) of pYEULC-S-AOD-9604 in SD medium (in the form of M-AOD-9604);

8. YEPD medium (1% Yeast Extract, 2% Bacto-peptone, 2% D-glucose) as negative control; and 9. SD medium (2% D-glucose, 0.67% Yeast Nitrogen Base without amino acids), as negative control.

Approximately 30 mg of freeze-dried YEpFlag-AOD-9604 and approximately 0.03–0.3 mg of freeze-dried pYEULC S-0AOD-9604-derived material was obtained, as estimated by dot blot analysis of antibody binding using Flag antibody M2 or rabbit polyclonal antibody against AOD-9604, measured compared to blots of serial dilutions of standard synthetic peptide of known concentration. Flag-AOD-9604-generated material was estimated to be of the order of 100 mg/liter by M2 (anti-Flag hybridisation), and 0.3–3 mg/liter for pYEULC-S-AOD-9604.

Preliminary in vitro lipolysis experiments showed lipolytic activity when adipose tissue from an ob/ob mouse was incubated with extracts of the preparations, diluted to an equivalent predicted 0.5 micromolar active molecule concentration based on the qualitative concentrations of active ingredient given above. Methodology followed for the in vitro tests was as desribed in M. A. Heffernan et al, "Effects of oral administration of a synthetic fragment of human growth hormone on lipid metabolism", Am J Physiol Endocrinol Metab 279: E501–E507, 2000.

It is similarly expected that the other peptides produced according to this example will have in vitro activity. As AOD9604 has already been shown to have in vitro activity in rodent, human, pig and dog tissue, and in vivo oral activity in all mammalian species tested (rodent and pig), it is therefore expected that foods made according to the invention, containing additional amino acids at either terminus such as those described in this example, will also have oral activity, either by direct oral bioavailability or indirectly via partial digestion to shorter orally bioavailable peptides closer in size to AOD9604.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited in the Example are listed on the following page.

REFERENCES

Macreadie, I. et al Biotech. Letters 1992, 14, 639–642
Macreadie, I. and Vaughan, P.
Recent Advances in Biotech. and Bioeng. 1998, 1, 465–479)
Sambrook, J., Fritsch, E. F., and Maniatis, T.
Molecular Cloning: A Laboratory Manual (Cold Spring Harbor Laboratory Press) 2$^{nd}$ Edition, 1989
Vaughan, P. et al 1998 DNA and Cell Biol., 17 511–518

The invention claimed is:

1. A transgenic plant comprising a first exogenous nucleic acid molecule which encodes a peptide corresponding to a mammalian growth hormone fragment and comprising a disulphide bond, wherein said peptide includes amino acid residues 177–191 of human growth hormone, (amino acids 2–16 of SEQ ID NO:9), a subfragment thereof, or an analogue thereof, wherein the analogue varies at no more than three positions from SEQ ID NO:9 and wherein the analogue contains an arginine at the position corresponding to position 3 of SEQ ID NO:9, and wherein the analogue contains a glutamic acid at the position corresponding to position 11 of SEQ ID NO:9, with the provision that any analogue is not intact, full-length growth hormone polypeptide, and in which the peptide, subfragment, or analogue is orally active and has the ability to increase lipolysis or decrease lipogenesis in a mammal to which the transgenic plant or a part or product thereof is orally administered.

2. A transgenic plant according to claim 1, in which the peptide, subfragment or analogue has the ability to stimulate the activity of hormone-sensitive lipase, and to inhibit acetyl CoA carboxylase.

3. A transgenic plant according to claim 1, in which the peptide, subfragment or analogue has the ability to reduce lipogenic activity.

4. A transgenic plant according to claim 1, in which the peptide, subfragment or analogue has the ability to stimulate lipolysis.

5. A transgenic plant according to claim 1, in which the first exogenous nucleic acid molecule encodes a peptide comprising amino acids 7–14 of SEQ ID NO:9 (hGH 182–189).

6. A transgenic plant according to claim 1, in which the first exogenous nucleic acid molecule encodes a peptide consisting of a methionine residue immediately followed by the amino acids from positions 2–16 of SEQ ID NO:9 (hGH 177–191).

7. A transgenic plant according to claim 1, in which the first nucleic acid molecule is operably linked to a second exogenous nucleic acid molecule encoding a heterologous fusion partner which is a signal sequence for a secreted polypeptide or protein.

8. A transgenic plant according to claim 7, in which there is a nucleic acid sequence encoding a specific protease cleavage site between the fusion partner and the growth hormone fragment.

9. A transgenic plant according to claim 1, which is a fruit or vegetable plant.

10. A transgenic plant according to claim 9, which is a tomato, banana, or potato plant.

11. A transgenic plant according to claim 1, which is a starch-synthesizing or starch-storing plant.

12. A transgenic plant according to claim 11, which is a plant selected from the group consisting of rye, barley, oats, wheat, rice, maize, peas, canola, and cassava.

13. A food or beverage product for use as part of the diet of a mammal, which product is produced by or derived from a transgenic plant according to claim 1, and which product comprises the first exogenous nucleic acid molecule.

14. A method of reducing fat/lean ratio, increasing lipolysis, or decreasing lipogenesis comprising the step of administering a food or beverage product according to claim 13 as part of the diet of a mammal in need of such treatment.

15. A method according to claim 14, in which the food or beverage product is administered to domestic livestock raised for meat production to reduce the fat/lean ratio of the livestock.

16. Propagating material of the transgenic plant according to claim 1.

17. Seeds, leaves, shoots, fruit, or other parts of the transgenic plant according to claim 1.

18. The transgenic plant of claim 1, wherein the peptide is selected from the group consisting of SEQ ID NO:9, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, and SEQ ID NO:40.

* * * * *